United States Patent [19]

Breslow

[11] 4,247,474
[45] Jan. 27, 1981

[54] NITRILE IMINES

[75] Inventor: David S. Breslow, Wilmington, Del.

[73] Assignee: Hercules Incorporated, Wilmington, Del.

[21] Appl. No.: 646,309

[22] Filed: Jan. 2, 1976

Related U.S. Application Data

[60] Continuation of Ser. No. 453,664, Mar. 21, 1974, abandoned, which is a division of Ser. No. 131,824, Apr. 6, 1971, Pat. No. 3,832,399, which is a continuation-in-part of Ser. No. 720,430, Feb. 2, 1968, abandoned, which is a division of Ser. No. 447,887, Apr. 13, 1965, Pat. No. 3,418,285.

[51] Int. Cl.$^3$ .................. C07C 121/00; C07C 121/46; C07C 121/14; C07C 121/50
[52] U.S. Cl. .............................. 260/465 E; 260/464; 260/465.5 R
[58] Field of Search ............ 260/465.5 R, 464, 465 E, 260/465.5 A

[56] References Cited

U.S. PATENT DOCUMENTS

| | | | |
|---|---|---|---|
| 3,390,133 | 6/1968 | Breslow | 260/75 |
| 3,390,204 | 6/1968 | Breslow | 260/837 |
| 3,418,285 | 12/1968 | Breslow | 260/75 |
| 3,448,063 | 6/1969 | Breslow | 260/2 |
| 3,504,017 | 3/1970 | Breslow | 260/482 |
| 3,670,023 | 6/1972 | Breslow | 260/566 A |

OTHER PUBLICATIONS

Huisgen, Angewandte Chemie, International Edition in English, vol. 2 (1963), pp. 3, 16-21.

Primary Examiner—Joseph P. Brust
Attorney, Agent, or Firm—Marion C. Staves

[57] ABSTRACT

Disclosed are polyfunctional nitrile imines having the formula selected from $R\text{---}C\equiv N^{\oplus}\text{---}N^{\ominus}\text{---}R')_x$ and $R\text{---}N^{\ominus}\text{---}N^{\oplus}\equiv C\text{---}R'')_x$ where R is an alkylene, cycloalkylene, arylene, alkyl-arylene, arylene-dialkylene, alkylene-diarylene or cycloalkylene-dialkylene radical; R' is a hydrogen, alkyl, cycloalkyl, aryl, alkaryl, or aralkyl radical; R'' is an alkyl, cycloalkyl, aryl, alkaryl or aralkyl radical and x is greater than 1; and their hydrogen chloride salts having the formula selected from

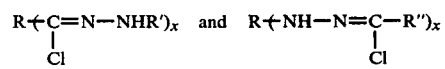

where R, R', R'' and x are as defined above.

3 Claims, No Drawings

NITRILE IMINES

This application is a continuation of U.S. Application Ser. No. 453,664 filed Mar. 21, 1974, now abandoned, which is a division of U.S. Application Ser. No. 131,824, filed Apr. 6, 1971, now U.S. Pat. No. 3,832,399, which is in turn a continuation-in-part of U.S. Application Ser. No. 720,430, filed Feb. 2, 1968 and now abandoned, which is in turn a division of U.S. Application Ser. No. 447,887, filed Apr. 13, 1965, now U.S. Pat. No. 3,418,285.

This invention relates to new compounds useful as cross-linking agents. More particularly, the invention relates to new polyfunctional nitrile imines.

In the past, cross-linking agents used in curing unsaturated polymers suffered from certain undesirable features. For example, some prior art agents are effective in cross-linking only at high temperatures, and are adversely affected by air and moisture.

Now, in accordance with this invention, it has been found that unsaturated polymers can be cross-linked with polyfunctional nitrile imines and their hydrogen chloride salts to produce tough, solvent-resistant, cross-linked products. The instant cross-linking agents can be used at moderate temperatures, and are not adversely affected by the presence of air and moisture.

The new polyfunctional nitrile imines of this invention have the formula selected from the group consisting of:

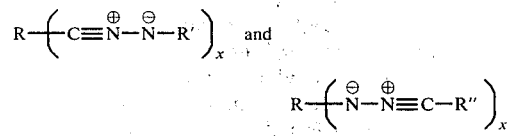

wherein R is an organic radical selected from the group consisting of alkylene radicals containing one to 20 carbon atoms such as methylene, dimethylene, trimethylene, tetramethylene, pentamethylene, hexamethylene, dodecamethylene, octamethylene, octadecamethylene, eicosylene and the like; arylene radicals having 1 to 3 rings such as o-, m- and p-phenylene, biphenylene, naphthylene and anthracenediyl and the like; cycloalkylene radicals containing 3 to 20 carbon atoms such as cyclohexylene, cyclooctylene, spiroheptylene, cyclopentylene, dicyclohexylene, cyclopropylene and cyclobutylene and the like; alkyl arylene radicals having $C_1$–$C_{20}$ alkyl radicals and 1 to 3 ring arylene radicals, such as 2,5-dimethyl-p-phenylene, 2-butyl-p-phenylene and 2-methyl-m-phenylene and the like; arylene-dialkylene radicals having $C_1$–$C_{20}$ alkylene radicals and 1 to 3 ring arylene radicals such as o-, m- and p-xylylene and o-, m- and p-phenylene-diethylene; alkylene-diarylene radicals having 1 to 3 ring arylene radicals and $C_1$–$C_{20}$ alkylene radicals such as methylene bis(o-, m- and p-phenyl), dimethylene bis(o-, m- and p-phenyl) and the like; and cycloalkylene-dialkylene radicals having $C_1$–$C_{20}$ alkylene radicals and 3 to 20 carbon atoms in the cycloalkylene radical such as 1,2-, 1,3- or 1,4-cyclohexane-dimethylene, 1,2- or 1,3-cyclopentane-dimethylene and the like; R' is selected from the group consisting of hydrogen, alkyl radicals containing one to 20 carbon atoms, such as methyl, butyl, nonyl, decyl, pentadecyl, eicosyl and the like; cycloalkyl radicals containing 3 to 20 carbon atoms, such as cyclopentyl, cyclooctyl, dicycloheptyl and cyclododecyl and the like; aryl radicals having 1 to 3 rings, such as phenyl, biphenyl and naphthyl radicals, alkaryl radicals having $C_1$–$C_{20}$ alkyl groups and 1 to 3 rings in the aryl group, such as methylphenyl, octadecylnaphthyl and the like; and aralkyl radicals having $C_1$–$C_{20}$ alkyl groups and 1 to 3 rings in the aryl group, such as benzyl, naphthylhexamethylene and the like; R'' is the same as R' except that it cannot be hydrogen; and x is an integer greater than 1. It will, of course be obvious to those skilled in the art that R can contain functional groups or substituents, which are substantially inert to the reactions in which these compounds are used, such as halides, ethers, thioethers, and the like.

The maximum value of x in the above general formula will be dependent on the number of carbon atoms in R, since x cannot, in any case, exceed the valence of R. Preferably, x will be an integer from 2 to 10. Of particular interest in this invention are the bis(nitrile imines) illustrated by general formulae I and II above wherein x is 2. It will be obvious to those skilled in the art that the nitrile imines of formulae I and II are equivalent.

Exemplary of the new polyfunctional nitrile imines of this invention are bis(nitrile imines) such as isophthalo-bis- (N-phenyl nitrile imine), terephthalo-bis(N-phenyl nitrile imine), isophthalo-bis(N-methyl nitrile imine), terephthalo-bis(N-methyl nitrile imine), isophthalo-bis(nitrile imine), terephthalo-bis- (N-ethyl nitrile imine), succino-bis(N-phenyl nitrile imine), adipo-bis(N-ethylnitrile imine), glutaro-bis(N-phenyl nitrile imine), 1,4- and 1,3-cyclohexane-bis(N-phenyl carbonitrile imine), N,N'-bis(benzylidyne)-1,4-dihydrazino benzene, and N,N'-bis(benzylidyne)-1,3-dihydrazinobenzene; phenylene-bis(dimethylene carbonitrile imine), tetramethylene-bis(p-phenylene N-butyl carbonitrile imine) and 1,3-cyclopentane-bis(trimethylene carbonitrile imine); and polyfunctional nitrile imines having more than two nitrile imine substituents such as trimeso-tris(N-phenyl nitrile imine), trimeso-tris(N-methyl nitrile imine), trimellito-tris(N-phenyl nitrile imine), trimellito-tris(N-ethyl nitrile imine, pyromellito-tetrakis(N-butyl nitrile imine), mellito-hexakis(N-phenyl nitrile imine).

The hydrogen chloride salts of the above-described nitrile imines are also very useful in the instant invention. These salts are polyfunctional hydrazide chlorides, and have the formula selected from the group consisting of:

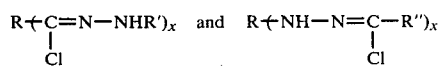

where R, R', R'' and x are as defined above in the description of the instant nitrile imines. It will be obvious that the hydrazide chlorides of the above formulae are equivalent.

Exemplary of the hydrogen chloride salts of the instant polyfunctional nitrile imines useful in this invention are bis-(hydrazide chlorides) such as isophthaloyl-bis(phenylhydrazide chloride), terephthaloyl-bis(phenylhydrazide chloride), isophthaloyl-bis(methylhydrazide chloride), isophthaloyl-bis(ethylhydrazide chloride), terephthaloyl-bis(methylhydrazide chloride), succinoyl-bis(phenylhydrazide chloride), adipoyl-bis(methylhydrazide chloride), p-phenylene dipropionyl-bis(methylhydrazide chloride), tetramethylene dibenzoyl-bis(butylhydrazide chloride), N,N'-p-phenylene-bis(- benzoyl hydrazide chloride), N,N'-m-phenylene-bis(benzoyl hydrazide chloride), glutaryl-bis(phenylhydrazide chloride), and 1,4-cyclohexane dicarboxyl-bis(phenylhydrazide chloride); and polyfunctional hydrazide chlorides containing more than two functional groups, such as trimesoyl-tris(phenylhydrazide chloride), trimesoyl-tris(methylhydrazide chloride), trimesoyl-tris(ethylhydrazide chloride), trimellitoyl-tris(phenylhydrazide chloride), trimellitoyl-tris(methylhydrazide chloride), pyromellitoyl-tetrakis(butylhydrazide chloride, benzenepentacarboxyl-pentakis(phenylhydrazide chloride), and mellitoyl-hexakis(phenylhydrazide chloride).

The polyfunctional nitrile imines of this invention are relatively unstable compounds, and the primary modes of cross-linking unsaturated polymers with these imines involves their formation in situ in a polymer mass from their closely related but more stable hydrogen chloride salts, i.e., the above-described polyfunctional hydrazide chlorides. This preparation of the nitrile imines from the hydrazide chlorides is usually accomplished by contacting the hydrazide chloride with an alkaline material. The reaction mechanism can be illustrated as follows:

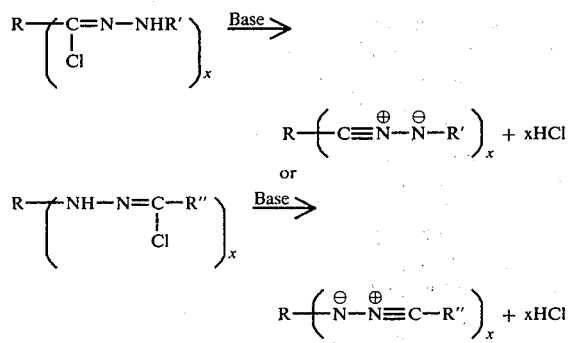

The basic or alkaline material which is used in this reaction can be a tertiary amine, alkali or alkaline earth metal hydroxide, alkali or alkaline earth metal salt such as carbonates or acetates or the like, or alkaline earth metal or zinc oxides.

The hydrogen chloride salts of the polyfunctional nitrile imines of this invention are themselves prepared by the reaction of phosphorus pentachloride with acyl or aroyl hydrazines. These acyl or aroyl hydrazines are prepared by the reaction of carboxylic acid chlorides with appropriately substituted hydrazines. The preparation mechanism for nitrile imines of formula I type can be illustrated as follows:

$R(COCl)_x + xH_2NNHR' \longrightarrow R(CONHNHR')_x + xHCl$ $R(CONHNHR')_x + xPCl_5 \longrightarrow$

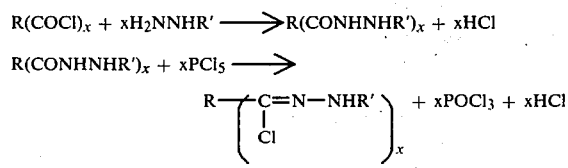

The preparation mechanism for nitrile imines of Formula II type can be illustrated as follows:

$R(NNH_2)_x^H + xR''COCl \longrightarrow R(NNHCOR'')_x^H + xHCl$ $R(NNHCOR'')_x^H + xPCl_5 \longrightarrow$

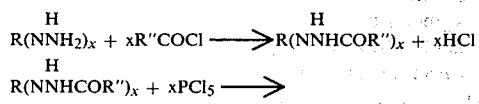

The preparation of the polyfunctional hydrazide chlorides of this invention will be further illustrated by the following examples. All parts and percentages referred to therein are by weight unless otherwise specifically indicated.

EXAMPLE 1

A solution of 20 parts of isophthaloyl chloride in 300 parts of chloroform is mixed with a solution of 42.5 parts of phenylhydrazine in 150 parts of chloroform over a period of one hour. The mixture is allowed to stand overnight, and the solid reaction product is then filtered, heated with water to remove salts, and then filtered again. The resulting product is dissolved in a mixture of dimethylformamide and water and recrystallized to yield 8.56 parts isophthaloyl-bis(phenylhydrazide) having a melting point of 269°-270° C.

A mixture of 12.2 parts of the isophthaloyl-bis(phenylhydrazide) so produced with 100 parts of diethyl ether and 17.9 parts of phosphorus pentachloride is refluxed for 21.5 hours. Then 30 parts of phenol in 35 parts of diethyl ether are added, followed by 25 parts methanol. The resulting solution is filtered and the solvent evaporated until crystallization begins. The solid product is recrystallized from a mixture of acetone and water and yields 4.26 parts of isophthaloyl-bis(phenylhydrazide chloride), melting point=167.5°-168.5° C. This product is analyzed for carbon, hydrogen and chlorine content, and the analytical results compared to the calculated amounts which should be present in $C_{20}H_{16}Cl_2N_4$. The calculated amounts are C, 62.67; H, 4.21; Cl, 18.5; amounts found on analysis are: C, 62.56; H, 4.85; Cl, 17.9.

EXAMPLE 2

The procedure of Example 1 is exactly duplicated, except that 20 parts of terephthaloyl chloride is substituted for the 20 parts of isophthaloyl chloride used in Example 1. The product so produced is 2.3 parts of terephthaloyl-bis(phenylhydrazide chloride), melting point=214.5°-215° C. This product is analyzed for carbon and hydrogen content, and the results are compared to amounts calculated for $C_{20}H_{16}Cl_2N_4$ as follows:

Calculated: C, 62.67; H, 4.21
Found on analysis: C, 62.74; H, 4.53.

EXAMPLE 3

A solution of 20 parts of adipoyl chloride in 300 parts of chloroform is mixed with a solution of 48 parts of phenylhydrazine in 150 parts of chloroform over a period of one hour. The solid reaction product is then filtered, heated with water to remove salts and then filtered again. The resulting product is recrystallized from a mixture of dimethylformamide and water to yield 12.3 parts of adipoyl-bis(phenylhydrazide).

A mixture of 10.0 parts of the adipoyl-bis(phenylhydrazide), so produced with 100 parts of diethyl ether and 19.0 parts of phosphorus pentachloride, is refluxed for 24 hours. Then 32 parts of phenol in 35 parts of diethyl ether is added, followed by 25 parts of methanol. The resulting solution is filtered and the solvent evaporated until crystallization begins. The solid product is recrystallized from a mixture of acetone and water to yield 3.1 parts of adipoyl-bis(phenylhydrazide chloride). This product is analyzed for carbon, hydrogen and chlorine content, and the amounts found on analysis compared to amounts calculated for $C_{18}H_{20}Cl_2N_4$ as follows:

Calculated: C, 57.91; H, 5.40; Cl, 19.00
Found on analysis: C, 58.10; H, 5.47; Cl, 18.90.

EXAMPLE 4

A solution of 20 parts of trimesoyl chloride in 450 ml. of chloroform is mixed with a solution of 50 parts of phenylhydrazine in 200 parts of chloroform over a period of 1.5 hours. The solid reaction product is then filtered, heated with water to remove salts, and then filtered again. The resulting product is dissolved in a mixture of dimethylformamide and water and recrystallized to yield 10.3 parts of trimesoyl-tris(phenylhydrazide).

A mixture of 10.0 parts of the trimesoyl-tris(phenylhydrazide) so produced, with 150 parts of diethyl ether and 15.0 parts of phosphorus pentachloride, is refluxed for 24 hours. Then 25 parts of phenol in 50 parts of diethyl ether is added, followed by 20 parts of methanol. The resulting solution is filtered and the solvent evaporated until crystallization begins. The solid product is recrystallized from a mixture of acetone and water to yield 2.7 parts of trimesoyl-tris(phenylhydrazide chloride). Analysis of this product shows the following:

Calculated amounts for $C_{27}H_{21}Cl_3N_6$: C, 60.51; H, 3.95; Cl, 19.85;
Amounts found on analysis: C, 60.39; H, 3.90; Cl, 20.01.

EXAMPLE 5

A mixture of 10 parts of benzoyl chloride in 100 parts of chloroform, 120 parts of water and 3.0 parts of sodium hydroxide is mixed with a solution of 4.92 parts of p-phenylene bis(hydrazine) in 50 parts of chloroform over a period of one hour. The solid reaction product is then filtered, heated with water, and then filtered again. The resulting product is recrystallized from a mixture of dimethylformamide and water to yield 6.4 parts of N,N'-p-phenylene bis(benzoyl hydrazide).

A mixture of 10.0 parts of the bis(benzoyl hydrazide) with 100 parts of diethyl ether and 15 parts of phosphorus pentachloride is refluxed for 24 hours. Then 25 parts of phenol in 50 parts of diethyl ether is added, followed by 21 parts of methanol. The resulting solution is filtered and the solvent evaporated until crystallization begins. The solid product is recrystallized from a mixture of acetone and water to yield 4.3 parts of N,N'-p-phenylene bis(benzoyl hydrazide chloride). This product was analyzed for carbon, hydrogen and chlorine content as follows:

Amounts calculated for $C_{20}H_{16}Cl_2N_4$: C, 62.67; H, 4.21; Cl, 18.50;
Amounts found on analysis: C, 62.81; H, 4.13; Cl, 18.62.

EXAMPLE 6

A solution of 10 parts of 1,4-cyclohexanedicarbonyl chloride in 200 parts of chloroform is mixed with a solution of 21 parts of phenylhydrazine in 75 parts of chloroform. The solid product is collected by filtration and washed with hot water to remove salts. The resulting material is then recrystallized from dimethylformamide and water to yield 5.9 parts of 1,4-cyclohexanedicarbonyl-bis(phenylhydrazide).

A mixture of 5 parts of the 1,4-cyclohexanedicarbonyl-bis(phenylhydrazide), 75 parts of diethyl ether and 6.9 parts of phosphorus pentachloride is refluxed for 21 hours. After adding a solution of 13 parts of phenol in 20 parts of ether, 15 parts of methyl alcohol is added. The resulting solution is filtered and the solvent evaporated until crystallization begins. The product is collected by filtration and then purified by recrystallization from acetone-water to yield 1.9 parts cyciohexanedicarbonyl-bis(phenylhydrazide chloride). The product is analyzed for carbon, hydrogen and chlorine as follows:

| Analysis | Found | Calculated for $C_{20}H_{22}Cl_2N_4$ |
|---|---|---|
| C | 62.1 | 61.8 |
| H | 5.88 | 5.66 |
| Cl | 17.8 | 18.2 |

EXAMPLE 7

A solution of 15 parts of 4,4'-methylenedibenzoyl chloride in 285 parts of chloroform is added to a solution of 22.2 parts of phenylhydrazine in 125 parts of chloroform. After stirring overnight, the solid product is collected by filtration and washed with hot water to remove salts. The resulting material is then recrystallized from dimethylformamide and water to give 9.1 parts of the 4,4'-methylenedibenzoyl-bis(phenylhydrazide).

A mixture of the above bis(phenylhydrazide) in 75 parts of diethyl ether and 7.15 parts of phosphorus pentachloride is refluxed for 22 hours. Then 14 parts of phenol in 25 parts of ether is added, followed by 15 parts of methyl alcohol. The reaction mixture is filtered and the ether solution concentrated until crystallization begins. The solid product is collected by filtration and recrystallized from a mixture of acetone-water to yield 2.1 parts of 4,4'-methylenedibenzoyl-bis(phenylhydrazide chloride). The product is analyzed for carbon, hydrogen and chlorine as follows:

| Analysis | Found | Calculated for $C_{27}H_{22}Cl_2N_4$ |
|---|---|---|
| C | 68.9 | 68.5 |
| H | 4.90 | 4.65 |
| Cl | 14.6 | 15.0 |

EXAMPLE 8

A mixture of 6.3 parts of benzoyl chloride in 70 parts of chloroform, 100 parts of water and 2.0 parts of sodium hydroxide is mixed with a solution of 4.5 parts of 2-methyl-1,4-naphthylene-bis(hydrazine) in 100 parts of chloroform. After stirring for 18 hours, the reaction mixture is filtered and the solid washed with hot water to remove salts. The resulting product is recrystallized from a mixture of dimethylformamide and water to yield 5.8 parts of 2-methyl-N-N'-1,4-naphthylene-bis(-benzoyl hydrazide).

A mixture of 5.0 parts of the above bis(benzoyl hydrazide) with 60 parts of diethyl ether and 5.9 parts of phosphorus pentachloride is refluxed for 24 hours. A solution of 10 parts of phenol in 25 parts of ether is then added, followed by 10 parts of methyl alcohol. The reaction mixture is concentrated until crystallization begins. The product is collected by filtration and recrystallized from acetone-water to yield 1.8 parts of 2-methyl-N,N'-1,4-naphthylene-bis(benzoyl hydrazide chloride) having the formula:

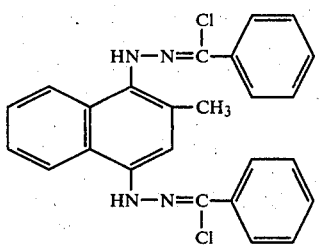

The product is analyzed for carbon, hydrogen and chlorine as follows:

| Analysis | Found | Calculated for $C_2H_{28}Cl_2N_4$ |
|---|---|---|
| C | 67.5 | 67.1 |
| H | 4.62 | 4.48 |
| Cl | 15.5 | 15.9 |

EXAMPLE 9

A mixture of 10.3 parts of benzoyl chloride in 75 parts of chloroform, 150 parts of water and 3.1 parts of sodium hydroxide is mixed with 8.3 parts of 4,4'-methylene-bis(phenylhydrazide) in 150 parts of chloroform. After stirring for 4 hours the reaction product is filtered and washed with hot water. A recrystallization from dimethylformamide and water yields 10.8 parts of 4,4'-methylene-bis(N-benzoylphenylhydrazide).

A mixture of 8.5 parts of the above bis(N-benzoylphenylhydrazide) with 80 parts of ether and 9.4 parts of phosphorus pentachloride is refluxed for 19 hours. A solution of 20 parts of phenol in 50 parts of ether is added, followed by 15 parts of methyl alcohol. The reaction mixture is then filtered and the clear solution concentrated until crystallization begins. The solid product is collected by filtration and recrystallized from acetone-water to yield 3.2 parts of 4,4'-methylene-bis(N-benzoylphenylhydrazide chloride) having the formula:

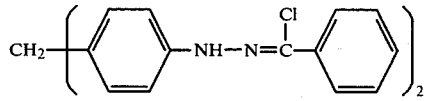

The product is analyzed for carbon, hydrogen and chlorine as follows:

| Analysis | Found | Calculated for $C_{27}H_{22}Cl_2N_4$ |
|---|---|---|
| C | 28.8 | 68.4 |
| H | 4.75 | 4.65 |
| Cl | 14.5 | 15.0 |

Other acyl and aroyl chlorides which can be reacted with phenyl hydrazine or other suitable hydrazines such as methylhydrazine, ethylhydrazine, cyclohexylhydrazine, benzylhydrazine and p-tolylhydrazine to produce the hydrazides include mellitoyl chloride, succinoyl chloride, glutaroyl chloride, malonoyl chloride and the like. The hydrazides resulting from that reaction are subsequently reacted with phosphorus pentachloride to produce the hydrazide chlorides or this invention. The former reaction can be carried out at room temperature, while the latter reaction should be carried out at a temperature between about 0°-100° C. Other suitable diluents may be substituted for those used in the above examples, as will be readily apparent to those skilled in the art.

As pointed out above, the polyfunctional hydrazide chlorides so produced are treated with a basic or alkaline material to produce the polyfunctional nitrile imines of this invention. Since the preferred formation of these nitrile imine cross-linking agents is in situ in the polymer mass, their preparation from their hydrogen chloride salts will be specifically illustrated along with the production of the cross-linked polymers in the examples set forth hereinafter.

The nitrile imines of this invention can also be prepared from polyfunctional tetrazoles, which on heating yield nitrogen and a nitrile imine, as shown by the following reaction mechanism:

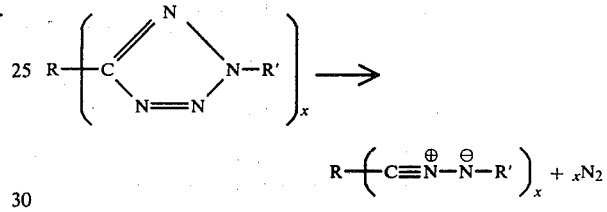

where R, R' and x are as defined above in the description of the instant nitrile imines. Polyfunctional tetrazoles are known in the art, and can be prepared, for example, by the reaction of aliphatic or aromatic polynitriles and alkali metal azides. As a further and more specific example, p-phenylene-bis-5-(2-phenyltetrazole) can be prepared by the reaction of terephthalaldehyde bis-(phenylhydrazone) and phenyl azide.

Suitable polyfunctional tetrazoles which can be used as nitrile imine precursors in accordance with this invention include tetramethylene bis-5-(tetrazole), p-phenylene bis-5-(tetrazole), hexamethylene bis-5-(tetrazole), and p-phenylene bis-5-(2-phenyltetrazole).

Generally, any type of unsaturated polymer, containing ethylenic unsaturation wherein there is at least one hydrogen radical attached to at least one of the carbon atoms of the double bond, can be cross-linked with the above-described polyfunctional nitrile imines and their hydrogen chloride salts, as described in parent application Ser. No. 447,887, now U.S. Pat. No. 3,418,285. Among the polymers which can be cross-linked in this manner are polybutadiene-1,2; polybutadiene-1,4; styrene—butadiene copolymers; butyl rubber (polyisobutylene—isoprene copolymers); natural rubber; polyester resins, such as, for example, maleate containing polyesters and polyacrylate esters; butadiene—acrylonitrile copolymers; ethylene—propylene—dicyclopentadiene terpolymers; polychloroprene; polyisoprene, alkyd resins such as, for example, tall oil alkyd resins; polyether copolymers and terpolymers containing at least one unsaturated epoxide constituent, such as, for example, propylene oxide—allyl glycidyl ether copolymer and ethylene oxide—epichlorohydrin—allyl glycidyl ether terpolymers; and other similar hydrocarbon or non-hydrocarbon unsaturated polymers. In addition to the above olefinically unsaturated polymers, polymers containing acetylenic unsaturation can be similarly cross-linked. Mixtures or blends of two or more of the above types of polymers may also be cross-linked.

The cross-linking is carried out by contacting the unsaturated polymer and a minor amount of the polyfunctional nitrile imine cross-linking agent for a time sufficient for the desired degree of cross-linking to occur. This uniform contacting is preferably achieved by uniformly mixing the polymer and the hydrogen chloride salt of the polyfunctional nitrile imine, and treating that mixture with an alkaline material, thereby generating the nitrile imine in situ in the polymer mass.

Alternatively, a polyfunctional tetrazole of the type described above can be uniformly incorporated in the polymer mass. When this tetrazole—polymer mixture is heated to a temperature above about 100° C., the polyfunctional tetrazole will break down, generating its corresponding polyfunctional nitrile imine and nitrogen gas, and the polyfunctional nitrile imine will thus uniformly contact the surrounding polymer mass, thereby initiating the cross-linking reaction.

The amount of polyfunctional nitrile imine cross-linker brought into contact with the unsaturated polymer will depend on the amount of cross-linking desired. While the polymer can be effectively contacted with from about 0.01% to about 50% by weight of the polymer of the hydrogen chloride salt of the polyfunctional nitrile imine, amounts between about 0.1% and 10% by weight of the polymer of that salt are preferred. Like amounts of polyfunctional tetrazole—precursor can also be used.

The rate of cross-linking will depend on the temperatures at which the unsaturated polymer and the polyfunctional nitrile imine are contacted. If the preferred procedure of adding the hydrogen chloride salt of the nitrile imine to the polymer is followed, very moderate temperatures can be used. Even contacting the polymer and cross-linking agent at room temperature produces highly satisfactory results. When using this method, temperatures between about 0°–200° C. are generally used, with temperatures between about 20°–100° C. being preferred. If the alternative method, using the tetrazole precursors, is used, temperatures between about 100°–300° C. must be used, with 150°–250° C. being preferred.

The uniform mixing of the unsaturated polymer with the hydrogen chloride salt of the instant nitrile imine or with the tetrazole precursor of the nitrile imine can be carried out by milling these ingredients on a conventional rubber mill, by dissolving the hydrogen chloride salt or the tetrazole precursor in a solvent solution of the polymer, or by any of other numerous methods, which will be readily apparent to those skilled in the art. This uniform contacting will result in the nitrile imine cross-linking agent being uniformly distributed throughout the polymer mass upon its in situ generation, so that uniform cross-linking can be achieved.

Additional ingredients can be incorporated in the polymer—salt or polymer—precursor blend, if desired. Common rubber additives such as, for example, extenders, fillers, pigments, plasticizers and stabilizers, can be included. In many cases, however, it will be more desirable to omit such additives and add only the hydrogen chloride salt of the polyfunctional nitrile imine or the tetrazole precursor of the polyfunctional nitrile imine to the unsaturated polymer.

The resulting cross-linked polymers are hard, tough rubbers, which are substantially insoluble in water and hydrocarbon solvents. They exhibit improved tensile properties over their uncured counterparts. These polymers are useful in various rubber applications, such as, for example, as protective and decorative coatings for various substrates including wood, metals, paper and plastics; as ingredients of tires for motor vehicles, tubing, pipe and other rubber articles; and the like.

The preparation of the instant cross-linked polymers will be further illustrated by the following specific examples. All parts and percentages referred to therein are by weight unless otherwise specifically indicated. The molecular weight of the polymers used in these examples is indicated by their Reduced Specific Viscosity. By the term "Reduced Specific Viscosity" (RSV0 is meant the $\eta$ sp/c determined on a 0.1% solution (0.1 gram of the polymer per 100 ml. of solution) of the polymer in a given solvent at the specified temperature.

EXAMPLE 10

In this example, 0.05 part of the isophthaloyl-bis(-phenylhydrazide chloride) prepared in Example 1 is uniformly mixed with a solution of 0.05 part of a maleate—isophthalate—propylene glycol polyester (Oronite Resin CR 19583, produced by the Oronite Chemical Co.), [RSV=0.09 in benzene at 25° C.] in 4 parts of acetone, and this mixture is evaporated to dryness at room temperature. The solid residue is treated with vapors of triethylamine for 1.5 hours at 25° C. The resulting product is a hard, tough material, substantially insoluble in acetone.

EXAMPLE 11

In this example, 0.05 part of the isophthaloyl-bis(-phenylhydrazide chloride) prepared in Example 1 is uniformly mixed with a solution of 1.0 part of a propylene oxide—allyl glycidyl ether copolymer (10% by weight of copolymer of allyl glycidyl ether) [RSV=5.2 in benzene at 25° C.] in about 20 parts of a benzene-—acetone solvent, and the resulting mixture is evaporated to dryness at room temperature. The solid rubber residue is treated with vapors of triethylamine for 5.0 hours at 30° C. The resulting product is a hard, tough rubber, substantially insoluble in chloroform.

The above procedure is exactly duplicated, except that no hydrazide chloride is added to the polymer solution. The rubber product so produced is completely soluble in chloroform.

EXAMPLE 12

In this example, 0.05 part of the terephthaloyl-bis(-phenylhydrazide chloride) prepared in Example 2 is uniformly mixed with a solution of 1.0 part of a propylene oxide—allyl glycidyl ether copolymer (10% by weight of copolymer of allyl glycidyl ether) [RSV=5.2 in benzene at 25° C.] in about 20 parts of benzene and the mixture is allowed to evaporate to dryness at room temperature. The solid residue is treated with vapors of triethylamine for 2.5 hours at 58° C. The resulting product is a hard, tough rubber, substantially insoluble in toluene.

EXAMPLE 13

In this example, 0.01 part of the adipolyl-bis(phenylhydrazide chloride) prepared in Example 3 is mixed with a solution of 1.0 part of 1,2-poly(butadiene) (RSV=3.2 in benzene at 25° C.) in 20 parts of benzene, and this mixture is evaporated to dryness at room temperature. The residue is treated with vapors of triethylamine for 3.0 hours at 60° C. The resulting product is substantially insoluble in toluene.

EXAMPLE 14

In this example, 0.005 part of the trimesoyl-tris(-phenylhydrazide chloride) prepared in Example 4, is mixed with a solution of 1.0 part of styrene—butadiene rubber (25 weight percent styrene, RSV=2.0 in benzene at 25° C.) in 30 parts of benzene and the resulting mixture is evaporated to dryness at room temperature. The solid rubber residue is treated with vapors of triethylamine for 8 hours at 60° C. The product is substantially insoluble in benzene.

EXAMPLE 15

In this example, 0.05 part of the bis(hydrazide chloride) prepared in Example 5 is mixed with a solution of 1.0 part of epichlorohydrin—ethylene oxide—allyl glycidyl ether terpolymer (60-30-10 weight percents, RSV=3.2 in alpha-chloronaphthalene at 100° C.) in 30 parts of acetone, and the resulting mixture is evaporated to dryness at room temperature. The solid rubber residue is treated with vapors of triethylamine for 8 hours at 65° C. The product is substantially insoluble in benzene.

What I claim and desire to protect by Letters Patent is:

1. A compound selected from the group consisting of a polyfunctional nitrile imine having the formula selected from the group consisting of

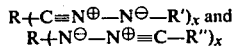 and
R—(N⊖—N⊕≡C—R")$_x$ wherein R is a radical selected from the group consisting of alkylene radicals selected from methylene, dimethylene, trimethylene, tetramethylene, pentamethylene, hexamethylene, octamethylene, dodecamethylene, and octadecamethylene radicals; cycloalkylene radicals selected from cyclobutylene, cyclopentylene, cyclohexylene, and cyclooctylene; arylene radicals selected from o-phenylene, m-phenylene, p-phenylene, biphenylene, and naphthylene; arylene-dialkylene radicals selected from o-xylylene, m-xylylene, p-xylylene, o-phenylene-diethylene, m-phenylene-diethylene and p-phenylene-diethylene; alkylene-diarylene radicals selected from methylene bis(o-phenyl), methylene bis(m-phenyl), methylene bis(p-phenyl), dimethylene bis(o-phenyl), dimethylene bis(m-phenyl) and dimethylene bis(p-phenyl); and cycloalkylene-dialkylene radicals selected from 1,2-cyclohexane-dimethylene, 1,3-cyclohexane-dimethylene, 1,4-cyclohexane-dimethylene, 1,2-dyclopentane-dimethylene and 1,3-cyclopentane-dimethylene; R' is a radical selected from the group consisting of hydrogen, $C_1$–$C_{20}$ alkyl radicals, $C_5$–$C_{12}$ cycloalkyl radicals, aryl radicals having 1 to 3 rings, alkaryl radicals having $C_1$–$C_{20}$ alkyl groups and 1 to 3 rings and aralkyl radicals having 1 to 3 rings and $C_1$–$C_{20}$ alkyl groups; R" is a radical selected from the group consisting of $C_1$–$C_{20}$ alkyl radicals, $C_5$–$C_{12}$ cycloalkyl radicals, aryl radicals having 1 to 3 rings, alkaryl radicals having $C_1$–$C_{20}$ alkyl groups and 1 to 3 rings and aralkyl radicals having 1 to 3 rings and $C_1$–$C_{20}$ alkyl groups; and x is an integer from 2 to 10.

2. The compound of claim 1 wherein the polyfunctional nitrile imine has the formula

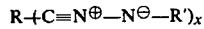

3. The compound of claim 2 wherein R is an arylene radical and R' is an aryl radical.

* * * * *

UNITED STATES PATENT AND TRADEMARK OFFICE
CERTIFICATE OF CORRECTION

PATENT NO. : 4,247,474
DATED : January 27, 1981
INVENTOR(S) : David S. Breslow

It is certified that error appears in the above-identified patent and that said Letters Patent are hereby corrected as shown below:

In the Abstract of Disclosure, line 2, " R--C " should read -- R$\neq$C --;

Col. 6, line 11 " cycio.... " should read -- cyclo.... --;

Col. 7, line 20 third column heading of the Table " $C_2H_{28}Cl_2N_4$ " should read -- $C_{25}H_{28}Cl_2N_4$ --;

Col. 8, line 1 " or " should read -- of --; and

Col. 10, line 14 " (RSVO " should read -- (RSV) --.

Signed and Sealed this

Twenty-eighth Day of April 1981

[SEAL]

Attest:

RENE D. TEGTMEYER

*Attesting Officer*  *Acting Commissioner of Patents and Trademarks*